United States Patent [19]

Kohayakawa

[11] Patent Number: 5,249,003
[45] Date of Patent: Sep. 28, 1993

[54] OCULAR REFRACTIVITY MEASURING APPARATUS

[75] Inventor: Yoshimi Kohayakawa, Yokohama, Japan

[73] Assignee: Canon Kabushiki Kaisha, Tokyo, Japan

[21] Appl. No.: 637,121

[22] Filed: Jan. 3, 1991

[30] Foreign Application Priority Data

Jan. 12, 1990 [JP] Japan ............... 2-005065
Mar. 1, 1990 [JP] Japan ............... 2-051360
Apr. 27, 1990 [JP] Japan ............... 2-112905
Apr. 27, 1990 [JP] Japan ............... 2-112906

[51] Int. Cl.$^5$ ............... A61B 3/10
[52] U.S. Cl. ............... 351/211; 351/214; 351/221
[58] Field of Search ............... 351/211, 205, 214, 221, 351/246

[56] References Cited

U.S. PATENT DOCUMENTS 4,650,301  3/1987  Humphrey ............... 351/211
4,755,041  7/1988  Ishikawa ............... 351/211

OTHER PUBLICATIONS

"Measurement of Ocular Refractive Power By A Planar Light Souce/Knife Edge Method", Kogaku (Optics), vol. 18, No. 10 (Oct. 1989) pp. 545–546.

Primary Examiner—Rodney B. Bovernick
Assistant Examiner—Hung Xuan Dang
Attorney, Agent, or Firm—Fitzpatrick, Cella, Harper & Scinto

[57] ABSTRACT

An ocular refractivity measuring apparatus includes a light receiving optical system, an illuminating optical system, an imaging device and a calculator. The light receiving optical system includes a light dividing member and an obturating plate. The obturating plate has a linear edge so as to obturate part of an opening of the light receiving optical system. The light dividing member is closer to a fundus of an eye to be measured in an optical path than the obturating plate. The illuminating optical system has a light source for projecting light in a direction perpendicular to the linear edge of the obturating plate, to the light dividing member so as to illuminate the fundus of the eye via the light dividing member. The imaging device is provided on a light receiving surface of the light receiving optical system at a position substantially conjugate with a pupil of the eye for detecting the amount of light in two regions of the pupil of the eye separated in a direction perpendicular to the linear edge of the obturating plate. The calculator calculates the refractivity of the eye in accordance with the ratio of the amount of light in the two regions of the pupil of the eye separated in a direction perpendicular to the linear edge detected by the imaging device and in accordance with the distance between the two regions.

10 Claims, 9 Drawing Sheets

OCULAR REFRACTIVITY MEASURING APPARATUS

BACKGROUND OF THE INVENTION

1. Field of the Invention

This invention relates to an improvement in an ocular refractivity measuring apparatus using a so-called photorefraction method.

2. Description of the Prior Art

A photorefraction method has been known which measures ocular refractivity from a shadow in a pupillary image of an eye to be measured. That is, on pages 545–546 in Kogaku (Optics) Volume 18, Number 10 (October, 1989), a method is disclosed in which a pupil is photographed, and ocular refractivity is estimated according to visual discrimination of a shadow in a pupillary zone, or is calculated using the gradient (the degree of inclination) of the shadow.

However, the accuracy of a conventional occular refractivity measuring apparatus using a photorefraction method is limited because it is influenced by the reflectivity of the fundus of an eye to be measured, and hence it has been difficult to obtain an exact measurement of ocular refractivity.

Furthermore, in a conventional ocular refractivity measuring apparatus using a photorefraction method, the entire apparatus must be moved to a focused position in the direction of the optical axis in order to have a clear pupillary image, and so the operation distance between an eye to be measured and the main body of the apparatus is limited. Hence, the apparatus has a poor operability because the entire apparatus must be moved.

Moreover, in a conventional apparatus, only ocular refractivity in a preset direction can be measured. If an eye to be measured has oblique astigmatism, its astigmatic angle, the degree of astigmatism and the degree of spherical ametropia cannot be measured.

SUMMARY OF THE INVENTION

It is an object of the present invention to provide an ocular refractivity measuring apparatus having a high accuracy using a photorefraction method.

It is another object of the present invention to provide an ocular refractivity measuring apparatus having an excellent operability using a photorefraction method.

It is still another object of the present invention to provide an ocular refractivity measuring apparatus which solves the above-described problems, and which can calculate the astigmatic angle, the degree of astigmatism, and the degree of spherical ametropia of an eye to be measured even if it has oblique astigmatism.

According to one aspect, the present invention which achieves these objectives, relates to an ocular refractivity measuring apparatus comprising a light receiving optical system, an illuminating optical system, an imaging device, and calculation means. The light receiving optical system comprises a light dividing member and an obturating plate having a linear edge so as to obturate part of an opening of the light receiving optical system. The light dividing member is closer to a fundus of an eye to be measured in an optical path than the obturating plate. The illuminating optical system has a light source member for projecting light to the light dividing member in a direction perpendicular to the linear edge for illuminating the fundus of the eye via the light dividing member. The imaging device is provided on a light receiving surface of the light receiving optical system at a position substantially conjugate with a pupil of the eye for detecting the amount of light in two regions of the pupil of the eye separated in a direction perpendicular to the linear edge of the obturating plate. The calculation means calculates the refractivity of the eye in accordance with the ratio of the amount of light in the two regions of the pupil of the eye separated in a direction perpendicular to the linear edge detected by the imaging device, and in accordance with the distance between the two regions. The light source member can have the shape of a slit, and the two regions can be point-like regions. The two regions can be separated from each other or can partially overlap each other. In addition, the distance between the two regions can be the distance between the centers of gravity of the two regions. Also, the calculation means can calculate the refractivity of the eye in accordance with the ratio of the total amount of light in the two regions or the average amount of light in the two regions.

According to still another aspect, the present invention which achieves these objectives relates to an ocular refractivity measuring apparatus comprising a focusing light receiving optical system, an illuminating optical system, an imaging device, magnification detection means, and calculation means. The focusing light receiving optical system comprises a light dividing member and an obturating plate having a linear edge so as to obturate a part of an opening of the focusing light receiving optical system. The light dividing member is closer to a fundus of an eye to be measured in an optical path than the obturating plate. The illuminating optical system has a light source member for projecting light to the light dividing member, in a direction perpendicular to the linear edge, for illuminating the fundus of the eye via the light dividing member. The imaging device is provided on a light receiving surface of the focusing light receiving optical system at a position substantially conjugate with a pupil of the eye. The magnification detection means detects a projection magnification for the pupil of the focusing light receiving optical system. The calculation means calculates the refractivity of the eye using outputs from the magnification detection means and the imaging device.

According to still another aspect, the present invention which achieves these objectives relates to an ocular refractivity measuring apparatus for illuminating an eye to be measured and for measuring the refractivity of the eye from a distribution of illuminance of pupillary images on an image medium by light beams obturated by an obturating plate having edges extending in two orthogonal directions at a position deviated from an optical axis and reflected by a fundus of the eye. The apparatus comprises an imaging optical system, an illuminating optical system, a light dividing member, and calculating means. The imaging optical system images the pupillary images on the image medium via the obturating plate having edges in two orthogonal directions at a position deviated from the optical axis. The illuminating optical system comprises two light sources. The system individually illuminates the eye to produce first and second pupillary images imaged by the imaging optical system using the two light sources. The two light sources extend in two directions perpendicular to the edges of the obturating plate. The light dividing member divides the light imaged by the imaging optical system and divides the light from the illuminating optical system. The calculating means calculates the astigmatic angle, the degree of astigmatism, and the degree of spherical ametropia of the eye by using the direction of a line segment, connecting two points on and passing through the center of the first pupillary image individually produced by one of the two light sources, along which the first pupillary image has the largest gradient of illuminance, by using the direction of a line segment, connecting two points on and passing through the center of the second pupillary image individually produced by the other of the two light sources, along which the second pupillary image has the largest gradient of illuminance, and by using the distribution of illuminance of the first and second pupillary images along the directions discussed above.

According to still another aspect, the present invention which achives these objectives relates to an ocular refractivity measuring apparatus for illuminating an eye to be measured and for measuring the ocular refractivity of the eye from a distribution of illuminance on a pupillary image imaged on an image medium by light beams obturated by an obturating plate having edges extending in two orthogonal directions and reflected by a fundus of the eye. The apparatus comprises an imaging optical system, an illuminating optical system, a light dividing member, and calculation means. The imaging optical system images the pupillary image on the image medium via the obturating plate. The illuminating optical system comprises two simultaneously lit light sources for illuminating the eye using the two light sources. The two light sources extend in two directions perpendicular to the edges of the obturating plate. The light dividing member divides light imaged by the imaging optical system and divides light from the illuminating optical system. The calculation means calculates the ocular refractivity of the eye in two directions, each perpendicular to a different one of the edges of the obturating plate, by using the distribution of illuminance of the pupillary image on the image medium in two directions, each perpendicular to a different one of the edges of the obturating plate.

According to still another aspect, the present invention which achieves these objectives relates to an ocular refractivity measuring apparatus comprising a light receiving optical system, an illuminating optical system, an imaging device, and calculation means. The light receiving optical system comprises a light dividing member and an obturating plate having a linear edge so as to obturate part of an opening of the light receiving optical system. The light dividing member is closer to a fundus of an eye to be measured in an optical path than an obturating plate. The illuminating optical system has an optical axis non-coaxial with the optical axis of the light receiving optical system. The illuminating optical system includes a light source member for projecting light to the light dividing member in a direction perpendicular to the linear edge of the obturating plate, for illuminating the fundus of the eye via the light dividing member. The imaging device is provided on a light receiving surface of the light receiving optical system at a position substantially conjugate with a pupil of the eye, for detecting the amount of light in two regions of the pupil of the eye separated by a predetermined distance in a direction perpendicular to the linear edge of the obturating plate. The calculating means calculates the refractivity of the eye in accordance with the ratio of the amount of light in the two regions of the pupil of the eye separated by the predetermined distance in a direction perpendicular to the linear edge of the obturating plate detected by the imaging device.

DESCRIPTION OF THE PREFERRED EMBODIMENTS

Figure 1:
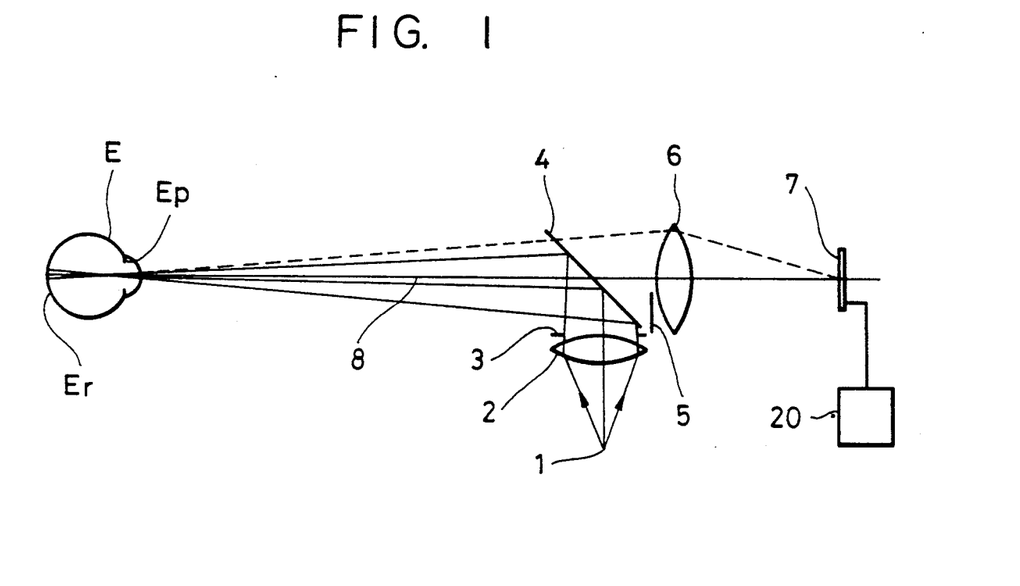
FIG. 1 is a diagram showing a first embodiment of the present invention.

FIG. 1 shows a first embodiment of the present invention. In the optical path 8 from the fundus Er of an eye E to be measured are provided a half-mirror 4, an obturating plate 5, a lens 6 and an imaging device 7 conjugate with the pupil Ep of the eye relative to the lens 6 in this order from the side of the eye. There is also shown an arithmetic unit 20.

Figure 3:
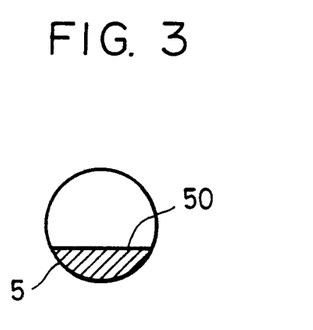
FIG. 3 shows an obturating plate in a light receiving system.

As shown in FIG. 3, the obturating plate 5 has a linear edge 50 so as to obturate part of the opening of the optical system. In FIG. 1, the upper end of the obturating plate 5 indicates the linear edge 50. In FIG. 1, if the direction connecting the upper end of the obturating plate 5 and the center of the pupil Ep of the eye is assumed to be the direction of the main light beam, an obturating plate 3, a lens 2 and a pointlike light source 1 are provided in this order from the eye on the optical path in the direction of the main light beam reflected by the half-mirror 4.

Figure 2:
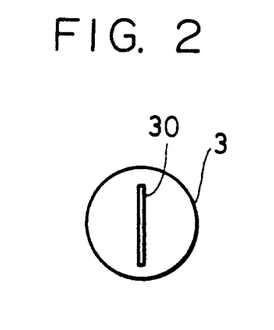
FIG. 2 shows an obturating plate in a projection system.

The obturating plate 3 is provided conjugate with the obturating plate 5 relative to the half-mirror 4. Although not essential, it is preferred that these two members are conjugate with each other. The obturating plate 3 has a slender slit opening 30 perpendicular to the direction of the linear edge 50, as shown in FIG. 2. FIG.

Figure 5:
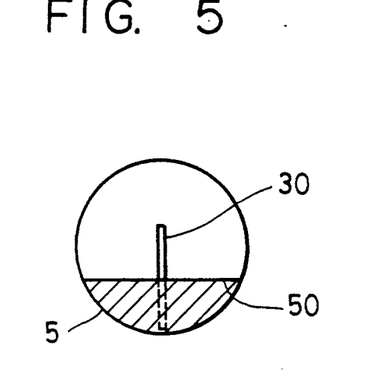
FIG. 5 is a diagram showing how the obturating plate in the projection system and the obturating plate in the light receiving system are arranged relative to each other.

5 shows the arrangement of the the obturating plates 3 and 5, as seen from the side of the eye E.

In FIG. 1, the pointlike light source 1 is imaged on the center of the pupil Ep of the eye by the lens 2, and the fundus Er of the eye is illuminated in the form of a slit by the slit opening 30.

Figure 4:
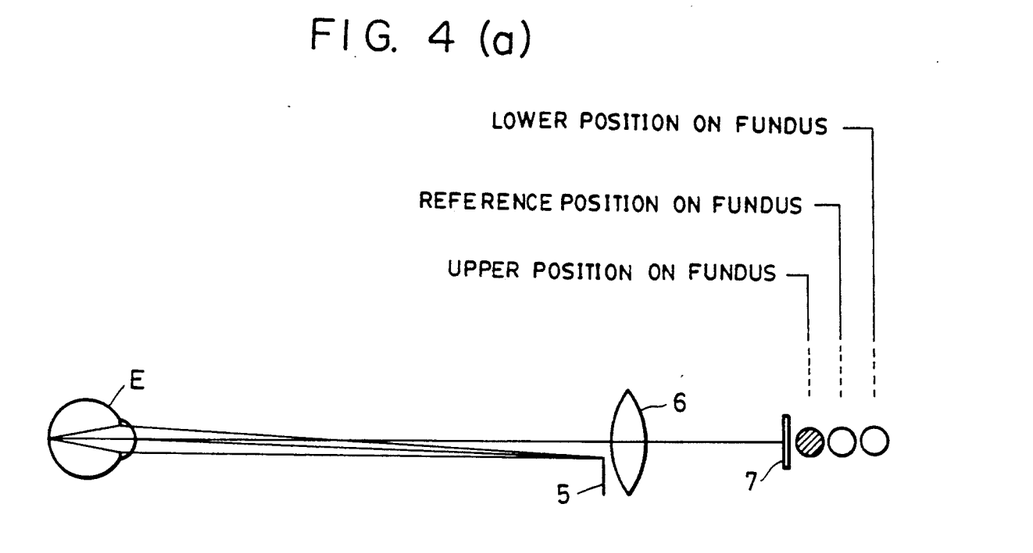
FIGS. 4(a)–4(c) are diagrams each showing how light beams reflected from a fundus are obturated by the obturating plate.

FIGS. 4(a)–4(c) show light beams reflected from the fundus Er of the eye. FIG. 4(a), which represents the case wherein the fundus Er of the eye and the obturating plate 5 are conjugate with each other, shows a state of the eye close to ametropia. A light beam from a reference position on the fundus of the eye corresponding to the upper end of the obturating plate 5 passes through the pupil of the eye, and reaches the imaging device 7 without being obturated by the obturating plate 5. A light beam from a position lower than the reference position on the fundus similarly passes through the pupil of the eye, and reaches the imaging device 7 without being obturated by the obturating plate 5. A light beam from a position above the reference position on the fundus is entirely obturated by the obturating plate 5. In summing up, the amount of light, that is illuminances, in two regions (for example, an upper position and a lower position) within the pupil of the eye detected on the imaging device 7 conjugate with the pupil of the eye have an identical value.

FIG. 4(b) represents the case wherein the fundus Er of the eye and a position closer to the eye than the obturating plate 5 are conjugate with each other. A light beam from the reference position on the fundus of the eye corresponding to the upper end of the obturating plate 5 passes through the pupil of the eye, and the lower half of the light beam is obturated by the obturating plate 5. Hence, the upper half of the pupil of the eye is darkened. The light beam is inverted in the horizontal and vertical directions by the lens 6, and is detected by the imaging device 7 so that the lower half of the pupil is darkened.

A light beam from a position lower than the reference position on the fundus, that is, a position below the optical axis, is obturated by the obturating plate 5 so that the degree of obturation of the light beam becomes smaller, after being first imaged. Hence, only a small portion of the upper end side of the pupil of the eye is darkened. The light beam is inverted in the horizontal and vertical directions by the lens 6, and is detected by the imaging device 7 so that only a small portion of the lower end side of the pupil is darkened. A light beam from a position above the reference position on the fundus is obturated by the obturating plate 5 so that the degree of obturation of the light beam becomes larger. Hence, only a small portion of the lower end side of the pupil of the eye is lightened. The light beam is inverted in the horizontal and vertical directions by the lens 6, and is detected by the imaging device 7 so that only a small portion of the upper end side of the pupil is lightened. In summing up, a distribution of illuminance on the imaging device 7 is obtained in which the amount of light is largest on the uppermost position, then linearly decreases toward the lower side, and is smallest on the lowermost position.

FIG. 4(c) represents the case wherein the fundus Er of the eye and a position farther from the eye than the obturating plate 5 are conjugate with each other. A light beam from the reference position on the fundus of the eye corresponding to the upper end of the obturating plate 5 passes through the pupil of the eye, and the lower half of the light beam is obturated by the obturating plate 5. Hence, the lower half of the pupil of the eye is darkened. The light beam is inverted in the horizontal and vertical directions by the lens 6, and is detected by the imaging device 7 so that the upper half of the pupil is darkened.

A light beam from a position lower than the reference position on the fundus is detected by the imaging device 7 so that only a small portion of the upper end side of the pupil is darkened.

A light beam from a position above the reference position on the fundus is detected by the imaging device 7 so that only a small portion of the lower end side of the pupil is lightened.

In summing up, a distribution of illuminance on the imaging device 7 is obtained in which the amount of light is largest on the lowermost position, then linearly decreases toward the upper side, and is smallest on the uppermost position.

Figure 6:
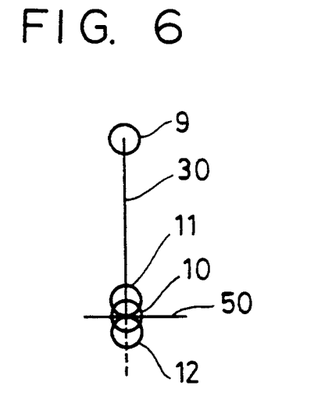
FIG. 6 is a diagram illustrating light beams from respective points on the fundus defocused on the surface of the obturating plate in the light receiving system.

FIG. 6 shows defocused circles on the surface of the obturating plate 5 representing light beams reflected from respective points on the image of the split 30 projected on the fundus. Circle 9 represents a light beam from an end portion of the image of the slit 30 projected on the fundus. Circle 10 represents a light beam from the above-described reference position.

Circle 11 represents a light beam which contacts the linear edge 50 and is not obturated by the obturating plate 5. Circle 12 represents a light beam which contacts the linear edge 50 and is entirely obturated by the obturating plate 5.

Figure 8:
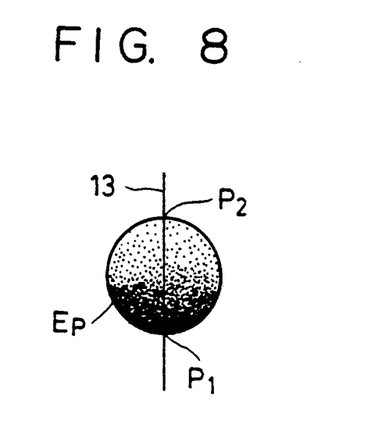
FIG. 8 is a diagram showing the pupillary image.

The pupillary image on the imaging device 7 obtained as described above is shown in FIG. 8.

Figure 9:
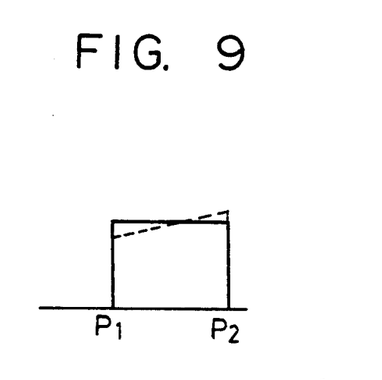
FIG. 9 is a diagram showing distribution of illuminance on the pupillary image.

The distribution of illuminance along center line 13 of the pupillary image is shown in FIG. 9. The ordinate represents the illuminance and the abscissa represents the distance from point $P_1$. The solid line, representing the case wherein the fundus and the obturating plate 5 are conjugate with each other, has a rectangular distribution. The broken line, representing the case wherein the fundus and the obturating plate 5 are not conjugate with each other, has a distribution having a slope. The diopter D of the eye is expressed by:

$$D = 2lD_0/d \times (1-A)/(1+A),$$

where A is the ratio of illuminance $a_1$ to $a_2$ of respective points $P_1$ and $P_2$, $D_0$ is the diopter corresponding to the position of the obturating plate 5, l is the length of the optical image of the slit at the opening measured from the linear edge 50, and d is the distance between the points $P_1$ and $P_2$.

If contrast is represented by B, the diopter D is also expressed by:

$$D = 2lD_0/d \times B,$$

where $A = a_1/a_2$ and $B = (a_1 - a_2)/(a_1 + a_2)$.

Figure 7:
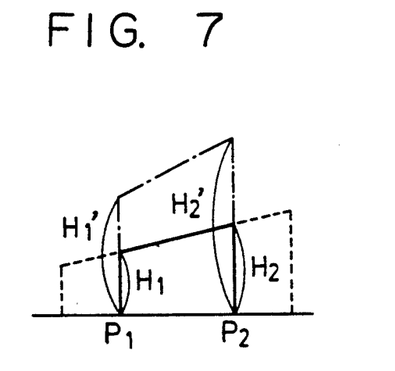
FIG. 7 is a diagram showing distributions of illuminance on a pupillary image when a pupil becomes larger, and when the reflectivity of the fundus is high.

FIG. 7 shows how the distribution of illuminance shown in FIG. 9 changes when the pupil becomes large and when the reflectivity of the fundus is high. The ordinate represents the illuminance and the abscissa represents the distance along center line 13 of the pupillary image.

The broken lines represents the case when the pupil becomes large, and the one-dot chain lines represent the case when the reflectivity of the fundus is high.

In FIG. 7, if the reflectivity of the fundus changes, the gradient of the slope changes even if ocular refractivity is constant. Hence, the measurement of the gradient of the slope does not exactly correspond to the measurement of the ocular refractivity.

That is, if both illuminances $H_1$ and $H_2$ of the respective points $P_1$ and $P_2$ are multipled by K (K is a constant) to become $H'_1$ and $H'_2$, the gradient of the slope clearly changes.

However, if the points $P_1$ and $P_2$, separate by a certain distance, are determined on the image surface and the ratio of illuminance or contrast is measured, as in the present embodiment, the measured data can exactly correspond to the measurement of the ocular refractivity irrespective of changes in the reflectivity of the fundus since the ratio of $H'_1$ to $H'_2$ has the same value as the ratio of $H_1$ to $H_2$.

If a space is present between the upper distal end of the slit opening 30 and the linear edge 50 in FIG. 5, the defocused light beam 9 can pass through the slit opening 30 without being obturated by the obturating plate 5, as shown in FIG. 6.

When the length of a portion of the slit opening 30 above the linear edge 50 is equal to the length of a portion of the slit opening 30 lower than the linear edge 50, and the absolute value of the length of a portion of slit opening 30 above linear edge 50 is equal to the distance from the upper distal end of the slit opening 30 to the upper end (the northern or uppermost position of the circle shown in FIG. 5) of the rim of the circular opening (which corresponds to the aperture diameter of the lens 6), linearity in the distribution of illuminance on the pupillary image is maintained over the widest range of diopter.

As shown in FIG. 5, it is preferred that the linear edge 50 is situated at a position lower than the central position of the circular light receiving opening. If the length of the portion of the slit opening 30 above the linear edge 50 is equal to the distance from the position where the slit opening 30 crosses the linear edge 50 to the position where the slit opening 30 crosses the rim of the circular opening in the horizontal direction, the circular light receiving opening is most effectively utilized. That is, when a semicircle (upper side) whose center is at a position where the slit opening 30 crosses the linear edge 50 is considered, light beams of a semicircle having the largest absolute value can pass under these conditions.

The above-described two conditions can be achieved by setting the length of the linear edge 50 to 80% of the circular light receiving opening shown in FIG. 5, that is, the aperture diameter of the lens 6.

The points $P_1$ and $P_2$ need not necessarily be situated at ends of the pupil and at positions symmetrical relative to the center of the pupil (for example, one point may be situated on the center of the pupil and the other point may be situated at a position not on the center of the pupil). In addition, the points $P_1$ and $P_2$ situated at symmetrical positions may not be on the center line. This is because the distribution of illuminance is identical to the above-described distribution of illuminance on an arbitrary line in a direction perpendicular to the linear edge 50.

Furthermore, the calculation of the illuminance ratio or contrast is not limited to point regions, such as $P_1$ and $P_2$, but may be performed for area regions having the points $P_1$ and $P_2$ as respective centers of gravity (the two regions may be separated from each other, or may partially overlap each other). In this case, the illuminance ratio or contrast between the two regions is calculated using the total amounts or average amounts of light of the area regions.

It is particularly effective to calculate the diopter D of the eye using the above-described expression by considering two area regions, i.e., the upper and lower halves of the pupil which are symmetrical relative to the center of the pupil, where d is the distance between the positions of the centers of gravity of the area regions, and A is the ratio between the total amounts or average amounts of light in the area regions.

Figure 10:
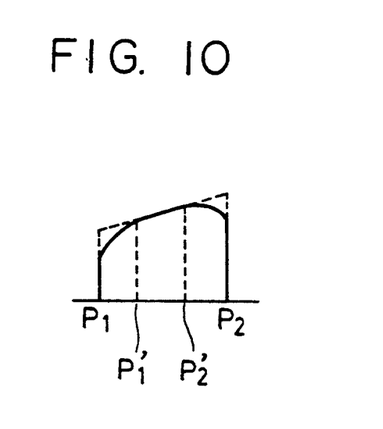
FIG. 10 is a diagram showing a distribution of illuminance on the pupillary image when the diopter of an eye to be measured is large.
Figure 11:
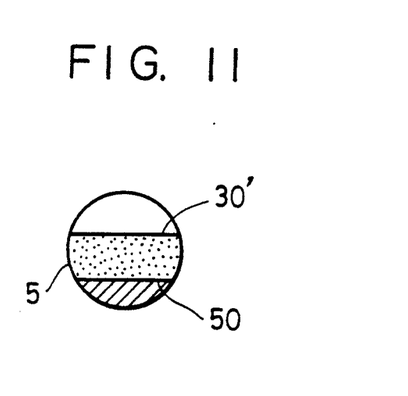
FIG. 11 is a diagram showing a modification of the obturating plate in the projection system and the obturating plate in the light receiving system.

As shown in FIG. 10, if the diopter of the eye is large, linearity in the illuminance distribution disappears at the end portions thereof. Hence, the illuminance ratio or contrast between points P1' and P2' situated within the range wherein linearity holds is calculated. Although, in the above explanation, it has been assumed that the opening of the obturating plate 3 has the shape of a slit, the width of the slit may be widened to the entire width of the opening of the lens, as represented by border line 30' (not limited to a straight line) shown in FIG. 11.

Although the light source 1 has been assumed to be a pointlike light source, a light source having an area so as to include the pupil Ep may also be used. Alternatively, instead of condensing light beams from a light source condensed by the lens 2, a diffusive light source may be provided at the position of the obturating plate 3.

Figure 12:
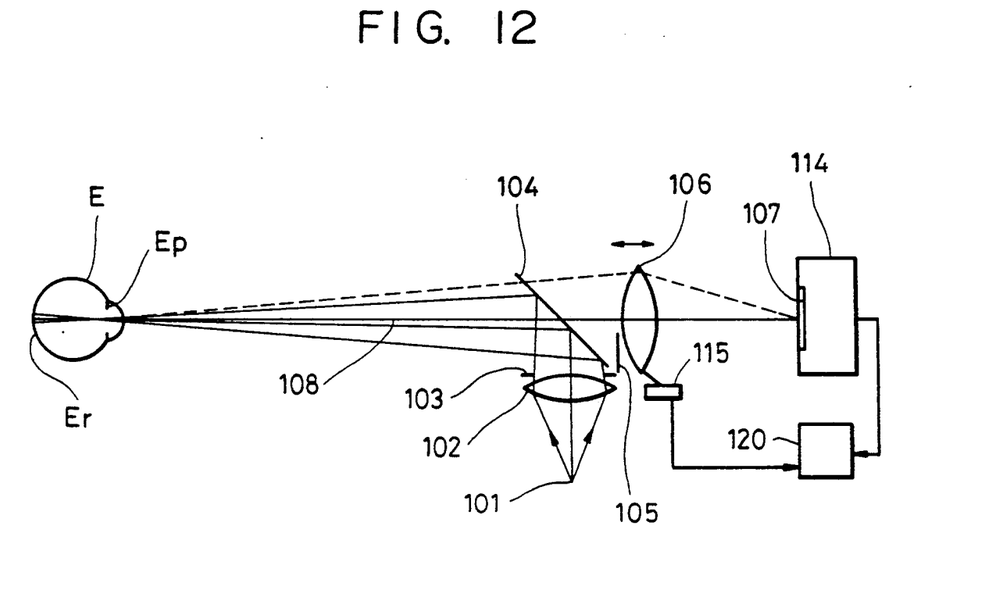
FIG. 12 is a diagram showing a second embodiment of the present invention.

FIG. 12 shows a second embodiment of the present invention which has excellent operability. In the optical path 108 from the fundus Er of an eye to be measured are provided a half-mirror 104, an obturating plate 105, a lens 106, an imaging device 107 conjugate with the lens 106 relative to the pupil Ep of the eye, and a video camera 114 in this order from the side of the eye. A pointlike light source 101 projects light through a lens 102 through a slit in an obturating plate 103 to half-mirror 104.

The lens 106 is focused in the direction of the two-head arrow by a lens driving unit 115. Information relative to the position of the lens 106 is input to an arithmetic unit 120, and the projection magnification of the pupil is detected.

In focusing, the lens 106 may be moved by hand. An output from the video camera 114 is input to the arithmetic unit 120 in addition to the position information of the lens 106. The arithmetic unit 120 calculates the ratio or contrast between the amounts of light in two regions of the pupil of the eye, and calculates the diffractivity of the eye according to the calculated data. When the lens 106 moves in focusing, the main body of the apparatus is fixed to an arbitrary position. The projection magnification of the pupil is calculated, for example, in the following way.

That is, the projection magnification of the pupil is expressed by:

$$M=x/(L-x)=x/f-1$$

from the expression $1/(L-x)+1/x=1/f$, where x (capable of being calculated by the arithmetic unit 120) is the distance between the lens 106 and the imaging device 107 in the direction of the optical axis 108, L (L is arbitrary) is the distance between the pupil of the eye and the imaging device 107 in the direction of the optical axis, and f is the focul length of the lens 106.

The lens 106 may be a fixed-focus lens, or a variable-focal-length lens, such as a zoom lens or the like.

The diopter D of the eye can be obtained using the expression described in the first embodiment. In the present embodiment, D=P/M, where M is the projection magnification of the pupil and P is the interval between two points under consideration on the imaging device 107.

Figure 13:
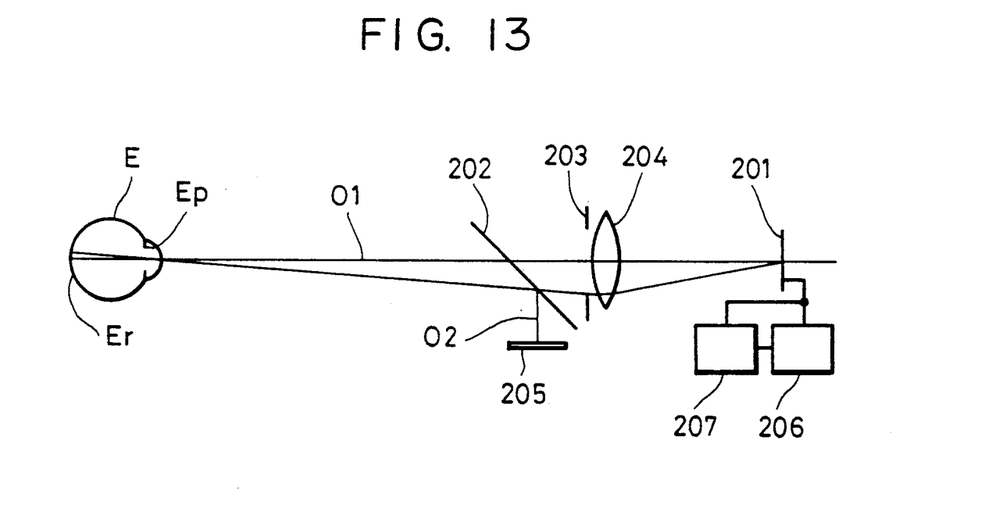
FIGS. 13 through 19 are diagrams showing a third embodiment of the present invention.
Figure 14:
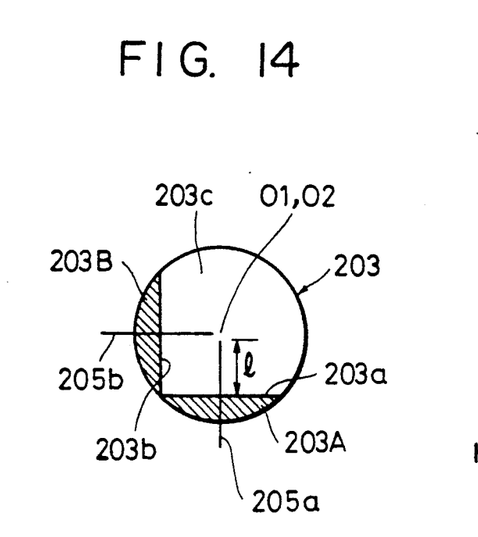

FIG. 13 shows a third embodiment of the present invention which can measure astigmatism. On the optical axis 01 from an eye E to be measured to an image medium 201, such as a charge coupled device (CCD) or the like, are successively arranged a half-mirror 202, an obturating plate 203 and a lens 204. As shown in FIG. 14, the obturating plate 203 comprises an obturating member 203A having a horizontal linear edge 203a situated at a position deviated from the optical axis 01, an obturating member 203B having a vertical linear edge 203b situated at a position also deviated from the optical axis 01, and an opening 203C situated around the optical axis 01. On the optical axis 02 in the direction reflected from the half-mirror 202 are provided linear light source 205 comprising light sources 205a and 205b disposed so as to be perpendicular to the edges 203a and 203b of the obturating plate 203, as shown in FIG. 14, and to be conjugate with the obturating plate 203, as shown in FIG. 14. The output from the image medium 201 is connected to an arithmetic circuit 206 and a frame memory 207.

In performing a measurement operation, pupillary images are imaged twice on the imaging medium 201 by individually, that is, not simultaneously, lighting the light sources 205a and 205b. Light beams from the light sources 205a and 205b are reflected by the half-mirror 202, and reach the fundus Er of the eye E. The light beams reflected by the fundus Er pass through the half-mirror 202, the obturating plate 203 and the lens 204, and the pupillary images are imaged on the image medium 201. If the positional relationship of the components in the apparatus is arranged so that the fundus Er of the eye E is not conjugate with the light source 205 and the obturating plate 203, light beams from respective points of the light source 205a or 205b reflected by the fundus Er become as follows. That is, if there is astigmatism in the eye E, the light beams are defocused in the shape of an ellipse at the position of the obturating plate 203 due to the refractivity of the eye. The ocular refractivity is measured by detecting the shape of the ellipse of the defocused light beams.

Figure 15:
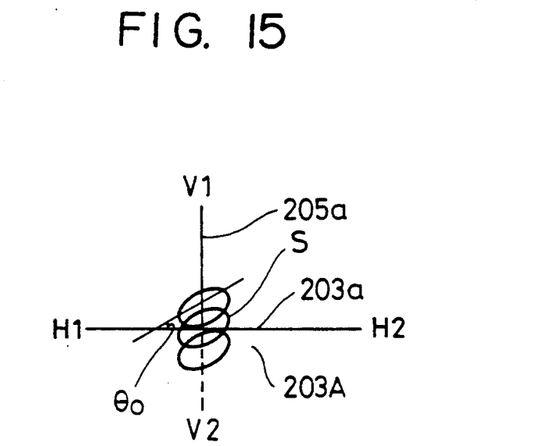

In general, the eye has oblique astigmatism, and so the directions of the major axis and the minor axis of the ellipse of the out of focus light beams need not necessarily coincide with the directions of the edges 203a and 203b. Hence, when only the light source 205a is lit, the out of focus light beams projected on near the edge 203a are a group of ellipses S making an astigmatic angle $\theta_0$ of the eye E with the edge 203a (as shown in FIG. 15), which are partially obturated by the obturating member 203A making the edge 203a, the border of obturation. The obturated area clearly depends on the astigmatic angle $\theta_0$, the length of the major axis, and the length of the minor axis, which represent the shape of the ellipse. A distribution of illuminance is produced in pupillary images on a circle on the image medium 201 depending on the obturated areas. When only the light source 205b is lit, an identical result is obtained relative to the edge 203b.

From the distributions of illuminance in the pupillary images when the light source 205a is first lit and the light source 205b is then lit, and from the astigmatic angle $\theta_0$ and the elliptic rate e based on the horizontal direction H1-H2 and the vertical direction V1-V2, the refractivity in the direction of the astigmatic angle $\theta_0$ and refractivity in the vertical direction can be calculated by the arithmetic circuit 206 using a method to be described later. When the pupillary images are imaged by a television camera, the calculation processing may be performed after performing A/D conversion of an image video signal and inputting the converted signal into the frame memory 207.

Figure 16:
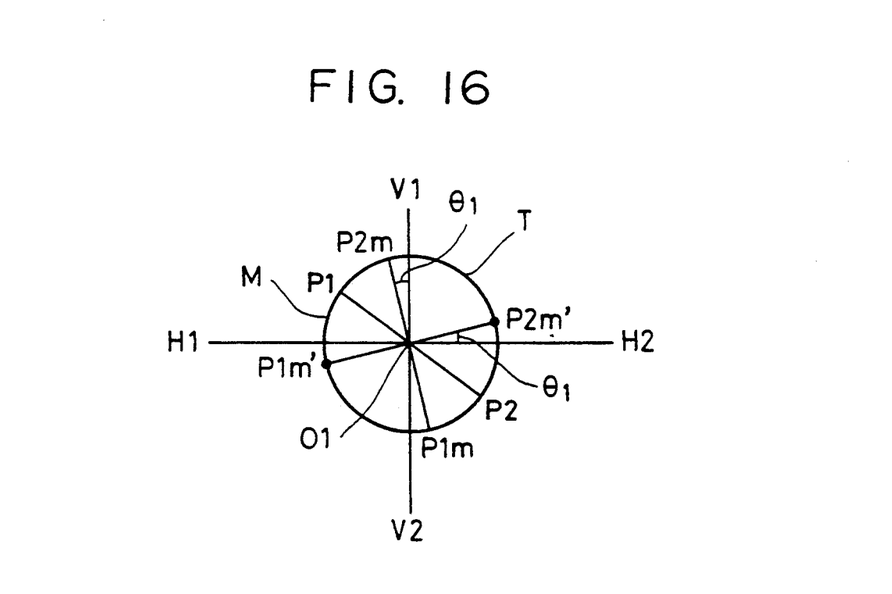
Figures 17, 18:
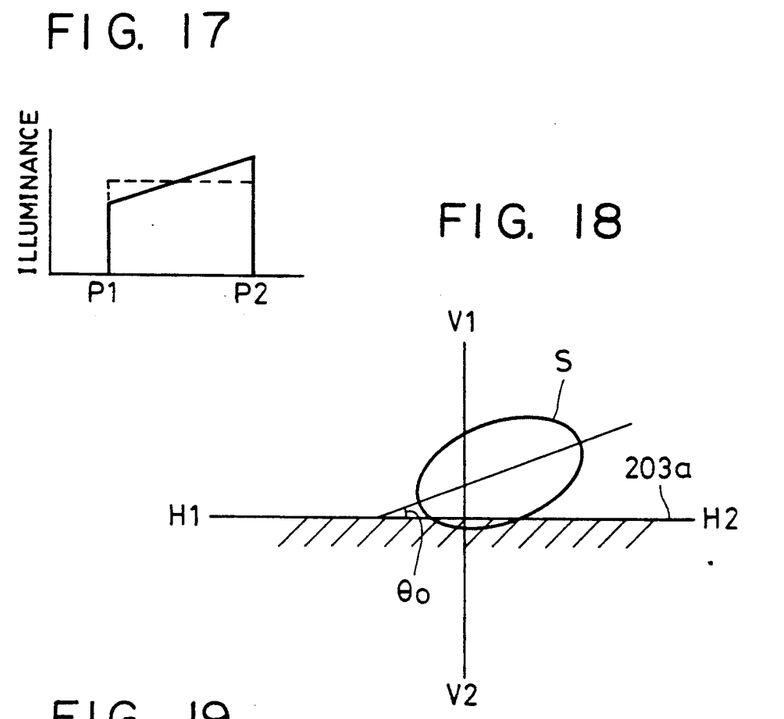

FIG. 16 shows a pupillary image M on the image medium 201 when only the light source 205a is lit. As described above, a distribution of illuminance is produced in the pupillary image M due to the fact that the elliptic light beams S are partially obturated by the edge 203a. Illuminance on points between points P1 and P2 on a center line in an arbitrary direction of a circle T having a diameter d and having the optical axis 01 as its center linearly changes with a constant gradient of illuminance, as shown in FIG. 17. The gradient of illuminance depends on how the two points P1 and P2 on a center line are provided, that is, on the angle made by the line segment connecting the two points P1 and P2 with respect to horizontal direction H1-H2 and vertical direction V1-V2, and the horizontal direction H1-H2. As the position of the ellipse S representing the defocused light beam descends relative to the edge 203a, the obturated area of the ellipse S increases upwardly in the vertical direction V1-V2 in FIG. 18. This increase corresponds to a decrease of the illuminance on the pupillar image M upwardly in the vertical direction V1-V2 in FIG. 16. Since the astigmatic angle $\theta_0$ depends on the direction of the line segment having the largest gradient of illuminance, it is possible to calculate the direction of the line segment from the gradient of illuminance, and to derive the astigmatic angle $\theta_0$ from the direction of the line segment. That is, the gradient of illuminance between two points P1 and P2 on an arbitrary center line of the circle T is calculated for every center line. If two points in the direction having the largest gradient of illuminance are represented by P1m and P2m, and if the angle made by the line segment P1m' P2m' perpendicular to the line segment P1m P2m and the horizontal direction H1-H2 is represented by $\theta_1$, the following expression (1) holds relative to the elliptic rate e of the ellipse S:

$$\tan \theta_0 = (1/e) \cdot \tan \theta_1 \tag{1}$$

An identical result may be obtained relative to the pupillary image when only the light source 205b is lit. Although not illustrated, two points Q1 and Q2 on an arbitrary center line of a circle T' having a diameter d and having the optical axis 01 as its center are considered. If the angle made by the line segment Q1m' Q2m' perpendicular to the line segment Q1m Q2m having the maximum gradient of illuminance is represented by $\theta_2$, the following expression (2) holds:

$$\tan (\theta_0 + 90°) = (1/e) \cdot \tan \theta_2 \tag{2}$$

Accordingly, the astigmatic angle $\theta_0$ and the elliptic rate e of the eye E can be calculated from the gradient of illiminance on the pupillar image M using the expressions (1) and (2).

Figure 19:
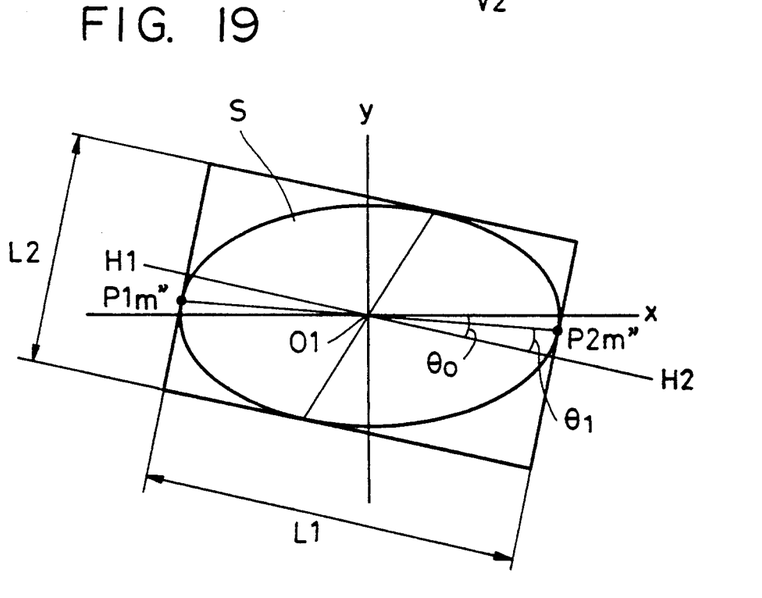

Next, the diffractivity of the eye E in the direction of the astigmatic angle $\theta_0$ and a direction perpendicular thereto will be calculated. Since a light beam reflected by the fundus Er is refracted in accordance with the refractivity to form the defocused ellipse S, the axis of the ellipse S in a certain direction is proportional to the refractivity of the eye E in that direction. That is, according to the ocular refractivity in a certain direction, the axis of the ellipse S in that direction is magnified or reduced. Accordingly, if the diameter of the ellipse S in a certain direction is represented by L, the diopter value D in that direction is proportional to the diameter L, and is expressed by the following expression (3):

$$D = -(L/d_0) \cdot D_0 \quad (3)$$

where $D_0$ is the reference diopter value at the position of the light source, and $d_0$ is the diameter of the pupil. Accordingly, in order to calculate the diopter value Da in the direction of the astigmatic angle $\theta_0$ of the eye E or the diopter value Db in a direction perpendicular thereto, which is the final objective, it is necessary to know the major diameter La or the minor diameter Lb of the ellipse S corresponding to the diameter L in the direction of the astigmatic angle $\theta_0$ or the direction perpendicular thereto of the ellipse S. However, the major diameter La and the minor diameter Lb cannot be directly calculated from the distribution of illuminance on the pupillary image M. Accordingly, as shown in FIG. 19, the diameter L1 in the horizontal direction H1–H2 and the diameter L2 in the vertical direction V1–V2 of the ellipse S are first calculated, and the major diameter La and the minor diameter Lb are derived using the two diameters L1 and L2. If the illuminance ratio and contrast between the two points P1m' and P2m' in the pupillary image M when only the light source 205a is lit are represented by A1 and B1, respectively, and the illuminance ratio and contrast between the two points Q1m' and Q2m' in the pupillary image M when only the light source 205b is lit are represented by A2 and B2, respectively, the diameters L1 and L2 are obtained by the following expressions (4)–(7). These illuminance ratios and contrasts may also be calculated from, for example, two regions. In this case, the distance between the centers of gravity of the regions may correspond to the interval between the two points in the above-described calculations.

$$L1 = \{(A1-1)/(A1+1)\} \cdot 2l \quad (4)$$

$$L1 = B1 \cdot 2l \quad (5)$$

$$L2 = \{(A2-1)/(A2+1)\} \cdot 2l \quad (6)$$

$$L2 = B2 \cdot 2l \quad (7)$$

In the above-described expressions, L is the length of the light sources 205a and 205b in portions at the side of the opening 203C. The relationship between the diameters L1, L2 and the major diameter La, the minor diameter Lb can be derived from the geometric relationship between these two types of diameters.

In FIG. 19, the ellipse S is depicted on the x-y orthogonal coordinate plane with the astigmatic angle $\theta_0$ coinciding with the x axis. The ellipse S is defined by expression (8) or expression (9) having angle $\theta$ as the parameter.

$$x^2/(4 \cdot La^2) + y^2/(4Lb^2) = 1 \quad (8)$$

$$x = (\tfrac{1}{2}) La \cdot \cos \theta$$

$$y = (\tfrac{1}{2}) Lb \cdot \sin \theta \quad (9)$$

In the ellipse S shown in FIG. 19, if the distance between two points P1m'' and P2m'' in the direction making an angle $\theta_1$ with the horizontal direction H1–H2 is represented by dp'', the above-described axis L1 of the pupillary image M is the projection of the line segment P1m'' P2m'' on the direction of the astigmatic angle $\theta_0$, and is expressed by the following expression (10). The direction dp'' is expressed by expression (11) calculated from the expression (9).

$$L1 = dp'' \cdot \cos(\theta_0 - \theta_1) \quad (10)$$

$$dp'' = (La^2 \cos^2\theta_1 + Lb^2 \sin^2\theta_1)^{\frac{1}{2}} \quad (11)$$

A similar relationship holds for two points Q1m'' and Q2m'' in the direction making an angle $\theta_2$ with the horizontal direction H1–on the ellipse S. If the distance between the two points Q1m'' and Q2m'' is represented by dq'', the following expressions (12) and (13) hold relative to the above-described axis L2 of the pupillary image M:

$$L2 = dq'' \cdot \cos(\theta_0 + 90 - \theta_2) \quad (12)$$

$$dq'' = (La^2 \cos^2\theta_2 + Lb^2 \sin^2\theta_2)^{\frac{1}{2}} \quad (13)$$

From these four expressions (10)–(13), the following expressions (14) and (15) for obtaining the major diameter La and the minor diameter Lb can be derived.

$$La^2 = \{L1^2 \cdot \sin^2\theta_2/\cos^2(\theta_2 - \theta_1) - \quad (14)$$

$$L2^2 \cdot \sin^2\theta_1/\sin^2(\theta_0 - \theta_2)\}/(\sin^2\theta_2\cos^2\theta_1 - \sin^2\theta_1\cos^2\theta_2)$$

$$Lb^2 = \{L1^2 \cdot \cos^2\theta_2/\cos^2(\theta_0 - \theta_1) - \quad (15)$$

$$L2^2 \cdot \sin^2\theta_1/\sin^2(\theta_0 - \theta_2)\}/(\sin^2\theta_1\cos^2\theta_1 - \sin^2\theta_2\cos^2\theta_1).$$

In summing up, the major diameter La and the minor diameter Lb of the ellipse S can be calculated from the illuminance ratios A1 and A2 or the contrasts B1 and B2 in the directions of the angles $\theta_1$ and $\theta_2$ on the pupillary image M, and the diopter values Da and Db in the direction of the astigmatic angle $\theta_0$ and the direction perpendicular thereto can finally be obtained according to expression (3).

Although, in the above-described embodiment, light beams passing through the center of the pupil Ep and illuminating the fundus Er have been considered, a nearly identical conclusion may be obtained for light beams passing through the entire pupil Ep. The light sources 205a and 205b are not limited to a linear shape, but slitlike light sources having a certain width may also be used. In order to exactly obtain the gradient of illuminance, it is desirable to arrange one ends of the light sources 205a and 205b near the optical axis 01 in the center of the opening 203C, and to pass all the defocused light beams therefrom through the opening 203C. It is preferred to extend the other ends of the light sources 205a and 205b to the reflection sides of the edges 203a and 203b to the same degree to obtain a pupillary image including the contribution from the extended portions. Hence, as the light sources 205a and 205b, it is suitable to provide a plurality of stroboscopic light sources or LEDs linearly arranged emitting light alternately.

Figures 20, 21, 22:
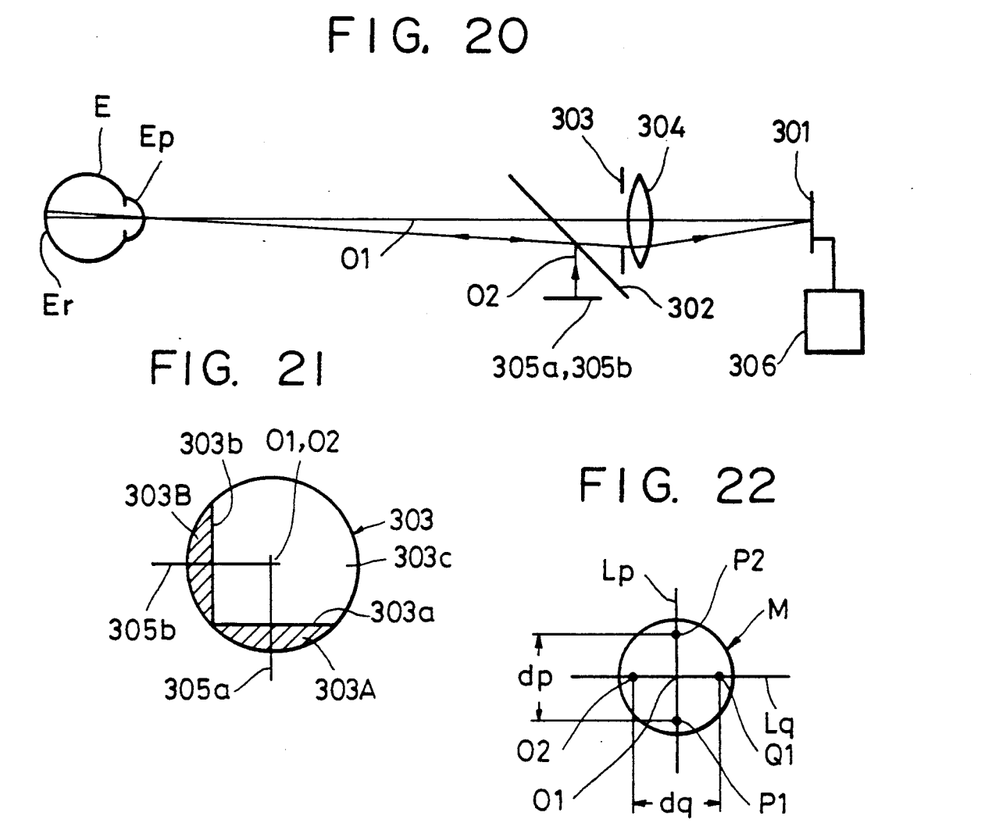
FIGS. 20–22, 23A, 23B, 24A, 24B, 25 and 26 are diagrams showing a fourth embodiment of the present invention.

FIG. 20 shows a fourth embodiment of the present invention in which two light sources perpendicular to each other are simultaneously lit. On the optical axis 01 from an eye E to be measured to an image medium 301, such as a charge coupled device (CCD) or the like, are provided an obliquely provided half-mirror 302, an obturating plate 303 and a lens 304 in order from the side close to the eye E. As shown in FIG. 21, the obturating plate 303 comprises an obturating member 303A having a linear edge 303a in the horizontal direction at a position deviated from the optical axis 01, an obturating member 303B having a linear edge 303b in the vertical direction at a position deviated from the optical axis 01, and an opening 303C consisting of the remaining portion. On the optical axis 02 in the direction reflected from the half-mirror 302 are arranged linear light sources 305a and 305b perpendicular to the edges 303a and 303b of the obturating plate 303, respectively, as shown in FIG. 22, at a position conjugate with the obturating plate 303. The output from the image medium 301 is connected to an arithmetic circuit 306.

Figure 23:
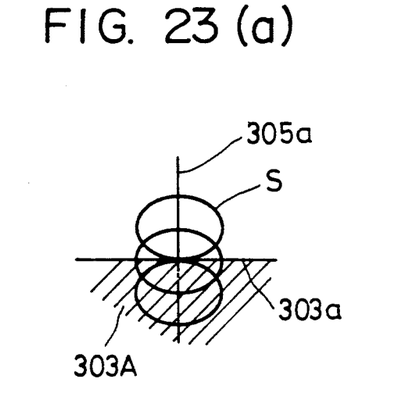
Figure 24A:
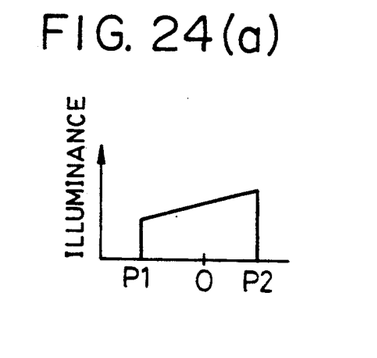
Figure 24B:
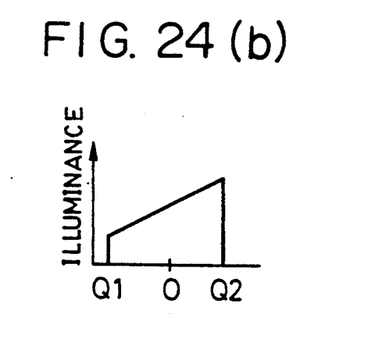

Light beams from the light sources 305a and 305b reflected by the half-mirror 302 enter the eye E. The light beams reflected by a fundus Er pass through the half-mirror 302, the obturating plate 303 and the lens 304, and a pupillary image M having the optical axis 01 as its center is imaged on the image medium 301, as shown in FIG. 22. If the position of the apparatus is set so that the fundus Er is not conjugate with the light sources 305a and 305b and the obturating plate 303, light beams from respective points of the light sources 305a and 305b reflected by the fundus Er are defocused in the shape of an ellipse at the position of the obturating plate 303 if the eye E has astigmatism. Defocused light beams S projected on near the edges 303a and 303b have shapes, for example, as shown in FIGS. 23(a) and 23(b), and are partially obturated by the obturating members 303A and 303B making the edges 303a and 303b the border of obturation. Accordingly, the illuminance on positions between two points P1 and P2 on vertical center line Lp of the pupillary image M or between two points Q1 and Q2 on horizontal center line Lq shown in FIG. 22 linearly changes due to the gradient of illuminance of the pupillary image M which depends on the ocular refractivity, as shown in FIG. 24(a) or FIG. 24(b).

By simultaneously lighting the light sources 305a and 305b, illuminance on the horizontal center line Lq or the vertical center line Lp includes a biasing component due to the light source 305b or 305a. Hence, a correction to subtract the biasing component, that is, ½ of the illuminance on the position of the optical axis 01, is performed. However, since the gradient of illuminance does not change even if the light sources 305a and 305b are simultaneously lit, it is unnecessary to correct the gradient of illuminance.

The diopter Dp on the vertical center line Lp making the position of the light source 305 a reference position is calculated by the following expression using the illuminance ratio Ap or the contrast Bp between the two points P1 and P2 after the correction. The illuminance ratio Ap and the contrast Bp may also be calculated, for example, from two regions. That is, the interval used in this case may be the distance between the centers of gravity of respective regions.

$$Dp = -(D_0/dp) \cdot 2lp \cdot (1 - Ap)/(1 + Ap)$$
$$= -(D_0/dp) \cdot 2lp \cdot Bp.$$

In the above-described expression, lp is the length of the light source 305a in a portion at the side of the optical axis 01 not overlapped with the obturating member 303A shown in FIG. 21, dp is the distance between the two points P1 and P2, and $D_0$ is the diopter value at the position of the light source. In a similar manner, the diopter value Dq on the horizontal center line Lq is calculated.

The gradient of illuminance depends on the reflectivity of the fundus, but does not depend on the diameter of the pupil. Ocular refractivities in two orthogonal directions independent from each other can be obtained by a single illumination and imaging operation. Hence, the present embodiment is effective particularly when measuring the ocular refractivity of an infant or the like whose pupillary image M easily moves. The calculation of the gradient of illuminance is facilitated if a regression line is first calculated from positions other than the four points P1, P2, Q1 and Q2 in which illuminance linearly changes.

In order to exactly obtain the gradient of illuminance, it is desirable to dispose one end of the light sources 305a and 305b near the optical axis 01 at the center of the opening 303C, and to pass all the defocused light beams therefrom through the opening 303C. Furthermore, it is preferred to extend the other ends of the light sources 305a and 305b to the reflection sides of the edges 303a and 303b to the same degree to obtain the pupillary image M including the contribution therefrom. Although, in the above-described embodiment, the gradient of illuminance between two points on the vertical center line Lp and the horizontal center line Lq has been used, the gradient of illuminance between two points in a direction perpendicular to the edges 303a and 303b may also be used if a correction for a biasing component is made.

Although, in the above-described embodiment, light beams passing through the center of the pupil Ep and illuminating the fundus Er are considered, an identical result may be obtained for light beams passing through the entire pupil Ep. When the pupillary image M is imaged by a television camera, calculation processing may be performed after performing A/D conversion of an image video signal and inputting the converted signal in a memory.

Figure 25:
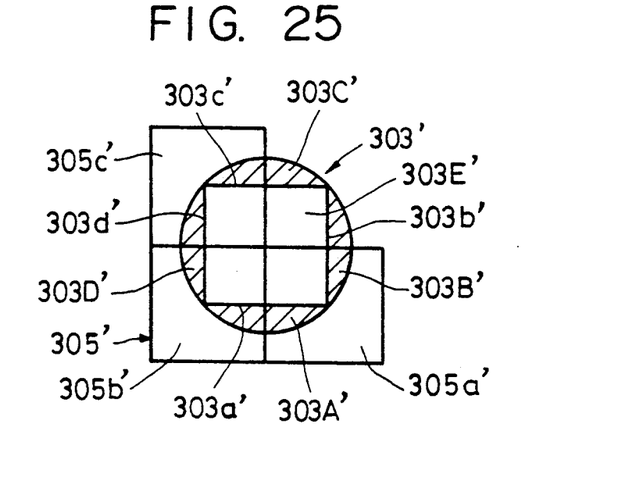

FIG. 25 shows a different embodiment, wherein an obturating plate 303' and a light source 305' are on the optical axes 01 and 02, respectively. The obturating plate 303' comprises obturating members 303A' and 303C' having linear edges 303a' and 303c' in the horizontal direction, respectively, obturating members 303B' and 303D' having linear edges 303b' and 303d' in the vertical direction, respectively, and an opening 303E' surrounded by these members. In place of linear light sources 305a and 305b, a light source 305', composed of three plate-like light sources 305a', 305b' and 305c', is provided so that the light sources 305a' and 305b' orthogonally intersect with the edges 303c' and 303d', and the light sources 305b' and 305c' orthogonally intersect the edges 303a' and 303b'. The amount of exit light from the light source 305b' is twice that of the light sources 305a' and 305c'. The respective positions of the obturating plate 303' and the light source 305' along the optical axes 01 and 02 and the other configuration are the same as in the foregoing embodiments.

Figure 26:
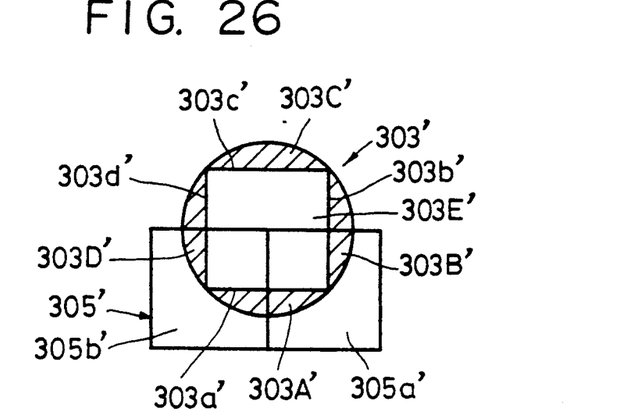

For the purpose of describing the principle of measurement of the present embodiment, a case in which the light source 305c' is retracted is shown in FIG. 26. If the light sources 305a' and 305b' are lit providing the same amount of light, this case corresponds to the same principle of measurement as when the light source 305a is lit in the FIG. 22 embodiment. That is, defocused light beams at the position of the obturating plate 303' are partially obturated by the edges 303a'–303c'. As a result, illuminance in the vertical direction linearly changes, and the ocular refractivity in the direction of the vertical center line Lp can be calculated from the gradient of illuminance.

The same principle holds also when the light source 305a' is retracted, and the light sources 305b' and 305c' are lit providing the same amount of light. Hence, ocular refractivities on the vertical center line Lp and the horizontal center line Lq are calculated using the light sources 305a'–305c' shown in FIG. 25, as when using the light sources 305a and 305b shown in FIG. 21. In addition, by using the light sources 305a'–305c' having an amount of exit light larger than that of the light sources 305a and 305b, it is possible to increase illuminance on the image medium 301, and to improve accuracy in measurement.

The individual components represented by block 20 shown in FIG. 1, by blocks 107, 114, 115 and 120 shown in FIG. 12, and by blocks 206 and 207 shown in FIG. 13 are well known in the ocular refractivity measuring art and their specific construction and operation is not critical to the operation or the best mode for carrying out the invention.

What is claimed is:

1. An ocular refractivity measuring apparatus comprising:
    a light receiving optical system comprising a light intensity dividing member and an obturating plate having a linear edge so as to obturate part of an opening of said light receiving optical system, wherein said light intensity dividing member is closer to an eye to be measured in an optical path than said obturating plate;
    an illuminating optical system having a light source member extending so that said light source member extending across the linear edge can be seen from the side of the eye for illuminating the fundus of the eye via said light intensity dividing member;
    an imaging device provided on a light receiving surface of said light receiving optical system at a position substantially conjugate with a pupil of the eye for receiving the light from said illuminating optical system via the eye for detecting the amount of light in two regions of the pupil of the eye arranged in a direction perpendicular to the linear edge; and
    calculation means for calculating the refractivity of the eye on the basis of one of the ratio of the amount of light in the two regions of the pupil of the eye arranged in a direction perpendicular to the linear edge detected by said imaging device and a quantity defined as the difference in the amount of light between the two regions divided by the amount of light in the two regions, and on the basis of the distance between the two regions.

2. An ocular refractivity measuring apparatus according to claim 1, wherein said light source member has the shape of a slit.

3. An ocular refractivity measuring apparatus according to claim 1, wherein the two regions are point-like regions.

4. An ocular refractivity measuring apparatus according to claim 1, wherein the two regions are separated from each other or partially overlap each other and wherein the distance between the two regions is the distance between the centers of gravity of the two regions.

5. An ocular refractivity measuring apparatus according to claim 4, wherein said calculation means calculates the refractivity of the eye in accordance with the ratio of the total amount of light in the two regions.

6. An ocular refractivity measuring apparatus according to claim 4, wherein said calculation means calculates the refractivity of the eye in accordance with the ratio of the average amount of light in the two regions.

7. An ocular refractivity measuring apparatus comprising:
    a focusing light receiving optical system comprising a light intensity dividing member and an obturating plate having a linear edge so as to obturate part of an opening of said focusing light receiving optical system, wherein said light intensity dividing member is closer to an eye to be measured in an optical path than said obturating plate;
    an illuminating optical system having a light source member extending so that said light source member extending across the linear edge can be seen from the side of the eye for illuminating the fundus of the eye via said light intensity dividing member;
    an imaging device provided on a light receiving surface of said focusing light receiving optical system at a position substantially conjugate with a pupil of the eye for receiving the light from said illuminating optical system via the eye;
    magnification detection means for detecting a projection magnification for the pupil of said focusing light receiving optical system; and
    calculation means for calculating refractivity of the eye using the output from said magnification detection means and on the basis of a distribution of illuminance of a pupillary image imaged on said imaging device.

8. An ocular refractivity measuring apparatus for illuminating an eye to be measured and for measuring the refractivity of the eye from a distribution of illuminance of pupillary images imaged on an image medium by light beams obturated by an obturating plate having edges extending in two orthogonal directions at a position deviated from an optical axis and reflected by a fundus of the eye, said apparatus comprising:
    an imaging optical system for imaging the pupillary image on the image medium via the obturating plate having edges in two orthogonal directions at a position deviated from the optical axis;
    an illuminating optical system, comprising two light sources for individually illuminating the eye to produce first and second pupillary images imaged by said imaging optical system using said two light sources, wherein said two light sources extend so that one of said two light sources extending across one of the edges of the obturating plate and the other of said two light sources extending across the other of the edges can be seen from the side of the eye in two directions perpendicular to the edges of the obturating plate;
    a light intensity dividing member positioned closer to the eye than said obturating plate, for directing the light so that light from said illuminating optical system is projected to the eye and imaged by said imaging optical system; and means for calculating an astigmatic angle, the degree of astigmatism, and the degree of spherical ametropia by using the direction of a line segment, connecting two points on and passing through the center of the first pupillary image individually produced by one of said two light sources, along which the first pupillary image has the largest gradient of illuminance, by using the direction of a line segment, connecting two points on and passing through the center of the second pupillary image individually produced by the other of said two light sources, along which the second pupillary image has the largest gradient of illuminance, and by using the distribution of illuminance of the first and second pupillary images along said directions.

9. An ocular refractivity measuring apparatus for illuminating an eye to be measured and for measuring the ocular refractivity of the eye from a distribution of illuminance on a pupillar image imaged on an image medium by light beams obturated by an obturating plate having edges extending in two orthogonal directions and reflected by a fundus of the eye, said apparatus comprising:

an imaging optical system for imaging the pupillary image on the image medium via the obturating plate;

an illuminating optical system, comprising two simultaneously lit light sources, for illuminating the eye using said two light sources, wherein said two light sources extend so that one of said two light sources extending across one of the edges of the obturating plate and the other of said two light sources extending across the other of the edges can be seen from the side of the eye;

a light intensity dividing member positioned closer to the eye than said obturating plate, for directing light so that light from said illuminating optical system is projected to the eye and imaged by said imaging optical system; and calculation means for calculating the ocular refractivity of the eye in two directions, each perpendicular to a different one of the edges of the obturating plate, by using the distribution of illuminance of the pupillary image on the image medium in two directions, each perpendicular to a different one of the edges of the obturating plate.

10. An ocular refractivity measuring apparatus comprising:

a light receiving optical system comprising a light intensity dividing member and an obturating plate having a linear edge so as to obturate part of an opening of said light receiving optical system, wherein said light dividing member is closer to an eye to be measured in an optical path than said obturating plate;

an illuminating optical system, having an optical axis non-coaxial with the optical axis of said light receiving optical system, including a light source member extending so that said light source member extending across the linear edge can be seen from the side of the eye for illuminating the fundus of the eye via said light intensity dividing member;

an imaging device provided on a light receiving surface of said light receiving optical system at a position substantially conjugate with a pupil of the eye for receiving the light from said illuminating optical system via the eye for detecting the amount of light in two regions of the pupil of the eye arranged by a predetermined distance in a direction perpendicular to the linear edge of said obturating plate; and calculation means for calculating the refractivity of the eye on the basis of one of the ratio of the amount of light in the two regions of the pupil of the eye arranged in a direction perpendicular to the linear edge of said obturating plate detected by said imaging device and a quantity defined as the difference in the amount of light between the two regions divided by the amount of light in the two regions.

* * * * *

UNITED STATES PATENT AND TRADEMARK OFFICE
CERTIFICATE OF CORRECTION

PATENT NO. : 5,249,003
DATED : September 28, 1993
INVENTOR(S) : YOSHIMI KOHAYAKAWA It is certified that error appears in the above-indentified patent and that said Letters Patent is hereby corrected as shown below:

COLUMN 6
Line 64, "represents" should read --represent--.

COLUMN 8
Line 64, "focul" should read --focal--.

COLUMN 10
Line 62, "illiminance" should read --illuminance--.

COLUMN 12
Line 13, "H1-on" should read --H1-H2 on--.

COLUMN 16
Line 63, "means for calculating" should begin a new paragraph.

Signed and Sealed this

Tenth Day of May, 1994

Attest:

BRUCE LEHMAN

Attesting Officer     Commissioner of Patents and Trademarks